United States Patent [19]

Forat et al.

[11] Patent Number: 5,493,054
[45] Date of Patent: Feb. 20, 1996

[54] PROCESS FOR THE SYNTHESIS OF ACID HALIDES AND REACTANTS USEFUL FOR ITS IMPLEMENTATION

[75] Inventors: Gerard Forat; Laurent Gilbert, both of Lyons, France

[73] Assignee: Rhone-Poulenc Chimie, Courbevoie, France

[21] Appl. No.: 313,402

[22] Filed: Sep. 27, 1994

Related U.S. Application Data

[63] Continuation of Ser. No. 10,322, Jan. 28, 1993, abandoned.

[30] Foreign Application Priority Data

Jan. 29, 1992 [FR] France ................................ 92 00964

[51] Int. Cl.⁶ .................................................. C07C 51/58
[52] U.S. Cl. ............................................................. 562/861
[58] Field of Search ............................................. 562/861

[56] References Cited

U.S. PATENT DOCUMENTS

| | | | |
|---|---|---|---|
| 1,963,748 | 6/1934 | Kyrides | 562/861 |
| 2,051,096 | 8/1936 | Mares | 562/861 |
| 4,623,491 | 11/1986 | Siegemund et al. | 562/852 |

FOREIGN PATENT DOCUMENTS

| | | |
|---|---|---|
| 0166293 | 1/1986 | European Pat. Off. . |
| 2066768 | 8/1971 | France . |
| 2704192 | 3/1978 | Germany . |
| 57-82336 | 5/1982 | Japan . |
| 926811 | 5/1963 | United Kingdom . |
| 1300918 | 12/1972 | United Kingdom . |

OTHER PUBLICATIONS

INPI Search Report dated Oct. 23, 1992.

*Primary Examiner*—Paul J. Killos
*Attorney, Agent, or Firm*—Finnegan, Henderson, Farabow, Garrett & Dunner

[57] ABSTRACT

The subject of the present invention is a new catalytic system and a process for the synthesis of acid halides, especially from haloforms. This process for halogenating by means of a haloform is characterized by the use of a metal chloride, advantageously trivalent, as a catalyst, the solubility of which in the reaction mixture is at least equal to one millimole, preferably 1/100 mole per liter, and the metal chloride also being at least half, advantageously two-thirds and preferably three-quarters in the dissolved state.

20 Claims, No Drawings

PROCESS FOR THE SYNTHESIS OF ACID HALIDES AND REACTANTS USEFUL FOR ITS IMPLEMENTATION

This application is a continuation of application Ser. No. 08/010,322, filed Jan. 28, 1993, now abandoned.

The subject of the present invention is a new catalytic system and a process for the synthesis of acid halides, especially from haloforms. It relates more particularly to a catalytic system and a process which makes it possible to replace oxyl functional groups with halide groups from haloforms substituted with a residue of nucleophilic nature.

Among the many techniques which make it possible to carry out the synthesis of acid halides, and more particularly of acid chlorides, it is suitable to mention those techniques which consist of ion exchange between phenylchloroform and the acid of which it is desired to form the chloride. For example, the use of Bronstedt acids has been proposed as a first step and then, the use of zinc chloride has been proposed as a second step. However, in very many cases, the reaction is either too slow, as in the case of Bronstedt acids, or leads to many impurities, especially to many heavy impurities. This is not desirable because there is formed, on the one hand, less of the desired acid chloride and, on the other hand, less benzoyl chloride, which can, in certain cases, constitute a value-enhanceable compound.

This is why one of the aims of the present invention is to provide a process which makes it possible to reconcile both a high reaction rate and the production of products with a good yield, which products are useful in various organic syntheses. Another aim of the present invention is to define a new catalytic system which allows low production of heavy impurities.

Another aim of the present invention is to provide a process which is capable of effecting the formation of acid chlorides from reputedly difficult derivatives such as, for example, the formation of trifluoroacetyl chloride from trifluoroacetic acid.

These aims and others, which will become apparent subsequently, are achieved by means of a halogenation process using a haloform in which a metal chloride, advantageously trivalent, is used as a catalyst, the solubility of which in the reaction mixture is at least equal to one millimole, preferably 1/100 mole per liter, and the said metal chloride being at least half, advantageously two-thirds and more preferably three-quarters soluble in the dissolved state.

It is desirable for there to be as little undissolved metal chloride as possible and for it to fall short of the thresholds above which its presence in the heterogeneous form in the reaction-bearing phase (that is to say, the phase which contains the reactants and where the reaction takes place) is easily detected.

It should be noted that the acid chlorides formed during the reaction help the dissolution in the reaction mixture and that it may be opportune to maintain an acid chloride content at least equal to one times, advantageously five times, and preferably ten times, that of the said metal chloride. This aspect is particularly advantageous when the invention is implemented continuously.

The metal chloride may be introduced directly or in a form capable of giving, in the reaction mixture, the same species as those formed by direct addition of the said metal chloride. For example, the preferred metal chloride, namely ferric chloride, may be introduced in the form of ferrous chloride since it is found in an oxidizing medium.

Advantageously, the said metal chloride is ferric chloride.

The threshold concentration of the said dissolved metal chloride at which the metal chloride shows a significant activity is 0.01% (or 100 ppm), expressed as a molar ratio as detailed below. Advantageously, the concentration of metal chloride is such that the concentration of metal chloride, expressed in moles per liter, and the concentration of a haloform functional group, preferably chloroform, expressed in gram equivalents per liter, wherein 2 gram equivalents equates to 1 mole, is between 0.02% and 5%, preferably between 0.1% and 1%.

It is preferable to work at relatively moderate temperatures. This is why a temperature is generally chosen between room temperature and 100° C. (in the present description, the positional zeros are not significant figures, unless specified). This limit may be brought to 200° C. when the haloforms are fluoroforms or when the reactants are generally reputed to be sluggish, as is the case with halogenating agents containing more than one haloform functional group on the same ring.

Advantageously, the temperature is between 30° C. and 100° C. and preferably between 50° C. and 80° C.

Pressure does not play an essential role but it is possible, in order to be able to recover one of the products of the reaction by means of a distillation during its formation, to be able to work at pressures which can vary between $10^3$ and $100.10^5$ and preferably between $10^4$ and $50.10^5$ Pascals.

The choice of pressure is determined by the choice of substrates and reactants as well as that which will be specified below.

The present invention is applicable to a large range of substrates.

In order to form the acid halide of formula R—COX, it is possible to start especially from a substrate of formula R—COO—R' where R is chosen from the group consisting of alkyl (preferably not carrying a double bond conjugated with the carbonyl functional group in order to avoid untimely polymerizations), aryl or aralkyl radicals and where R' is chosen from hydrogen, alkyl or acyl groups.

Where O—R' constitutes an oxyl group, the substrate advantageously forms an external, preferably symmetric, or internal anhydride.

Among the R radicals, it is appropriate to indicate that the invention is particularly useful in the case where the alkyls are perfluorinated ($R=R_F$).

Radicals are reputed to be perfluorinated when the first two carbons ($\alpha$ and $\beta$ positions of the carboxylic group or of the group which derives therefrom) are perfluorinated.

The alkyl, aryl, acyl and aralykl radicals described above and hereafter are not limited by the specific examples provided and shall be understood by one skilled in the art to include the broad range of substituents normally associated with such terms.

It is desirable for at least one of the acid halide(s), in general, chlorides, to be recovered during its formation. Those skilled in the art will recognize the application of LeChatelier's principle to the present invention. The present invention permits the formation of only one acid halide or one reactant in the medium because the other acid halide or reactant is being recovered and removed during formation. The present invention further permits the selection of operating conditions, especially pressure and the optional use of a solvent.

Also, when perfluoroacyl chlorides, and especially trifluoroacetyl chloride, are produced, it is advantageous to make use of the volatility which is characteristic of the strongly fluorinated derivatives and distill the acid chloride during formation.

This preference leads to a tendency towards substrates in which R has a boiling temperature at atmospheric pressure at most equal to 180° C.

As regards the choice of haloforms, chloroforms and bromoforms are preferred although the reaction is also possible with fluoroforms provided that the reaction is carried out at a higher temperature.

Thus, it is desirable for the chlorinating agent, namely chloroform, to be a compound, or a mixture of compounds, of formula Ar—CCl$_3$, where Ar is a residue having a doublet (i.e., a pair of electrons) or is unsaturated, and is in a position where it can stabilize a possible carbocation on the carbon atom of the haloform functional group. For instance, in the case where the doublet is in the form of an unsaturated bond, the chlorines of the chloroform functional group are, for example, and by order of preference, in the propargyl, allyl or benzyl position. Although the doublet can be conveyed by atoms such as halogens, preferably bromine and chlorine, or indeed other groups, unsaturated bonds are preferred, advantageously of the aryl type. Ar may thus be chosen from the ynyl, vinyl and aryl groups.

According to the present invention, it is highly preferable that the halogenating agent is always present in the reaction mixture in an amount at least equal to one times, advantageously five times, preferably ten times, that of the metal chloride.

This preferential condition leads to various advantageous embodiments.

When the production is batchwise, it is advantageous not to bring the reaction entirely to completion. This means that the reaction is halted as soon as the halogenating agent reaches a conversion threshold of 95% for the not very efficient catalysts or 99% for the efficient catalysts, such as ferric chloride.

When the process is carried out continuously, semicontinuously or noncontinuously, it is advantageous to introduce the reactant and the substrate in stoichiometric ratios. Thus, advantageously, the haloform is of formula Ar—CX$_3$, with X representing a halogen, preferably a bromine, a chlorine or a fluorine and most preferably ArCl$_3$.

The Ar group can itself carry other haloform functional groups which will also be reactive. Thus, it was shown during the study which led to the present invention that it was possible to produce phthalic acid chlorides from the corresponding chloroforms.

It may be recalled that the synthesis of orthodi(trichloromethyl)benzene is difficult, which reduces the economic importance of this technique for producing derivatives of orthophthalic acid.

In contrast, the process of the present invention is entirely usable for the synthesis of iso- and terephthalic acid chlorides.

Analysis of the results of the study which has led to the present invention showed that the haloforms which gave the most suitable reactions were the compounds which carried more than one chloroform functional group on the same ring, but that this was to the detriment of the reactivity. This loss of reactivity can be compensated for by an increase in the temperature. A good compromise must be found; therefore, it is preferable that the number of haloform functional groups does not exceed three on the same ring and preferably does not exceed two.

The distinct reactivity of the various haloform functional groups makes it possible to obtain compounds which have both acid halide and haloform functional groups, where the haloform functional groups are identical. In this illustration, the calculations relative to the compulsory or preferential conditions according to the present invention will only take into account the haloform functional groups for reaction purposes.

However advantageous it may be, this property has only a limited importance when the chloroforms are expensive or difficult to synthesize.

In general, it is preferred to use the substrates, the halogenating agents and the products resulting from the reaction themselves as the solvent. However, when these reactants are not liquid or do not form a liquid under the operating conditions, it may be advantageous to use a solvent, which can also be used for regulating the temperature, or even the pressure. The preferred solvents are chosen from the group consisting of those which have the following characteristics:

* relative inertia under the operating conditions;
* solubility of the said metal chloride at least equal to one millimole per liter, advantageously 1/100 mole per liter and preferably 1/10 mole per liter.

The reaction can be written:

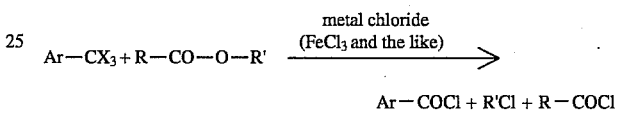

$$Ar—CX_3 + R—CO—O—R' \xrightarrow{\text{metal chloride (FeCl}_3\text{ and the like)}} Ar—COCl + R'Cl + R—COCl$$

One of the additional aims of the invention is to provide a reactant which is suitable for halogenating the substrates of formula R—COOR', where R is chosen from the alkyl (preferably not carrying double bonds conjugated with the carbonyl functional group in order to avoid untimely polymerizations), aryl or aralykl radicals and where R' is chosen from hydrogen, alkyl or acyl groups.

This aim is achieved using a reactant defined in that it contains a chloroform of formula Ar—CCl$_3$, where Ar is a residue having a doublet or is unsaturated, and is in a position where it can stabilize a possible carbocation on the carbon atom of the haloform functional group. For instance, in the case where the doublet is in the form of an unsaturated bond, the chlorines of the chloroform functional group are, for example and by order of preference, in the propargyl, allyl or benzyl position.

Although the doublets can be conveyed by atoms such as the halogens, preferably bromine and chlorine, or even ether groups, unsaturated bonds are preferred, advantageously of the aryl type. Ar may thus be chosen from the ynyl, vinyl and aryl groups. The reactant contains a ferric halide, chosen from the bromide and the chloride, at a concentration such that the ratio between that of the said halide, expressed in moles per liter, and that of the chloroform functional groups, expressed in equivalents per liter wherein 2 gram equivalents equates to one mole, is between 0.01% and 5%, preferably between 0.1% and 3%.

Halogenating agent and substrates rarely exceed 20 carbon atoms and even more rarely 50 carbon atoms.

The aryls are advantageously homocyclic (in contrast to heterocyclic) and do not contain more than four condensed or uncondensed rings.

The examples which follow are nonlimiting and illustrate the invention:

EXAMPLES

Reaction scheme

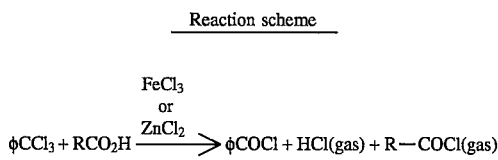

Example 1

107 g (0.54 mol) of phenylchloroform and 0.57 g of ferric chloride were charged into a 250 ml reactor under a nitrogen atmosphere, at 0° C. 62.5 g (0.548 mol) of trifluoroacetic acid were then charged in the reactor and the reactor was then closed on the homogeneous solution. The reactor was slowly heated so as to achieve a temperature of 60° C. after heating for 30 minutes. The pressure in the reactor was maintained between 7 and $8.10^5$ pascals by continuous removal of the gas phase. The reaction was continued for 130 minutes, emission of gas then ceasing. The volatile products were recovered by degassing, the assembly was then cooled and the equipment was purged using nitrogen. The nonvolatile products were recovered by distillation.

The conversion of the phenylchloroform was 100%.

The yield of trifluoroacetyl chloride was 98%.

The yield of benzoyl chloride was 93%.

The heavy products were obtained as traces.

Comparative Example

A similar test was carried out using zinc chloride (1.6 g) as the catalyst. The solubility of zinc chloride was less than 2000 ppm by weight. The reaction lasted five hours and the following results were obtained.

The conversion of the phenylchloroform was 81%.

The yield of trifluoroacetyl chloride was 70%.

The yield of benzoyl chloride was 78%.

2% of heavy products were obtained.

Example 2

The reaction was carried out in a 30 ml reactor at atmospheric pressure. An equimolar mixture of trifluoroacetic acid and phenylchloroform was continuously added to a solution of ferric chloride in benzoyl chloride at 65° C. (FeCl$_3$/(total øCCl$_3$ used)=0.15 molar %) for four and one half hours.

The volatile products formed (trifluoroacetyl chloride and hydrogen chloride) were continuously trapped and measured.

The following results were obtained:

Conversion of the phenylchloroform was 100%.

Yield of trifluoroacetyl chloride was 98.4%.

Yield of benzoyl chloride was 98.6%.

Example 3

The reaction was carried out as in Example 2 by adding one molar equivalent of phenylchloroform to a solution of ferric chloride in trifluoroacetic acid at 65° C. (FeCl$_3$/(total øCCl$_3$ used)=1.2 molar %) for 5 hours.

The following results were obtained:

Conversion of the phenylchloroform was 100%.

Yield of trifluoroacetyl chloride was 94.4%.

Yield of benzoyl chloride was 92.8%.

Example 4

The reaction was carried out as in Example 2 by adding one molar equivalent of trifluoroacetic acid to a solution of ferric chloride in phenylchloroform at 65° C. (FeCl$_3$/øCCl$_3$= 1.5 molar %) for four hours and ten minutes.

The following results were obtained:

Conversion of the phenylchloroform was 100%.

Yield of trifluoroacetyl chloride was 93.7%.

Yield of benzoyl chloride was 81.6%.

Other embodiments of the present invention will be apparent to those skilled in the art from consideration of the specification and practice of the present invention disclosed herein. It is intended that the specification and examples be considered as exemplary only, with a scope and spirit of the invention being indicated by the following claims.

What is claimed is:

1. A process for forming a perfluoro acid halide of formula R—COX comprising the steps of mixing together
   a haloform,
   a metal chloride,
   and a substrate to form a reaction mixture wherein said haloform is of the formula Ar—CX$_3$ wherein Ar is a residue having a doublet or an unsaturated bond in a position to stabilize a carbocation on the carbon atom of said haloform and wherein X is a halogen; wherein said metal chloride is trivalent and the solubility of said metal chloride in said reaction mixture is at least 1/100 mole per liter and wherein said metal chloride is at least ½ dissolved in said reaction mixture; and wherein said substrate is of the formula R—COOR', wherein R is perfluorinated and is selected from the group consisting of perfluoroalkyl, perfluoroaryl, and perfluoroaralkyl radicals and R' is selected from the group consisting of hydrogen, alkyl and acyl radicals.

2. The process of claim 1, wherein said metal chloride is at least ⅔ dissolved in said reaction mixture.

3. The process of claim 1, wherein said metal chloride is at least ¾ dissolved in said reaction mixture.

4. The process of claim 1, wherein said halogen is chlorine, bromine or fluorine.

5. The process of claim 1, wherein said Ar is selected from the group consisting of ynyl, vinyl and aryl radicals.

6. The process of claim 1, wherein said haloform is present in said reaction mixture at a content at least equal to one times that of said metal chloride.

7. The process of claim 6, wherein said haloform is present in said reaction mixture at a content at least equal to five times that of said metal chloride.

8. The process of claim 7, wherein said haloform is present in said reaction mixture at a content at least equal to ten times that of said metal chloride.

9. The process of claim 1, wherein said metal chloride is ferric chloride.

10. The process of claim 1, wherein the concentration of metal chloride is such that the ratio between the concentration of metal chloride, expressed in moles per liter, and the concentration of said haloform, expressed in gram equivalents per liter is between 0.01% and 5%.

11. The process of claim 10, wherein the concentration of metal chloride is such that the ratio between the concentration of metal chloride, expressed in moles per liter, and the concentration of said haloform, expressed in gram equivalents per liter is between 0.1% and 1%.

12. The process of claim 1 wherein said haloform is chloroform.

13. The process of claim 1, wherein said process occurs at a temperature between about 30° C. and about 100° C.

14. The process of claim 13, wherein said process occurs at a temperature between about 50° C. and about 80° C.

15. The process of claim 1, wherein R is perfluorinated and is a perfluoroalkyl radical.

16. The process of claim 1, wherein R is perfluorinated and is a perfluoroaryl radical.

17. The process of claim 1, wherein R is perfluorinated and is a perfluoroaralkyl radical.

18. The process of claim 1, wherein R' is hydrogen.

19. The process of claim 1, wherein R' is an alkyl radical.

20. The process of claim 1, wherein said substrate is trifluoroacetic acid.

* * * * *